US006520034B1

(12) United States Patent
Masquelier et al.

(10) Patent No.: US 6,520,034 B1
(45) Date of Patent: Feb. 18, 2003

(54) HIGH AIR VOLUME TO LOW LIQUID VOLUME AEROSOL COLLECTOR

(75) Inventors: Donald A. Masquelier, Tracy, CA (US); Fred P. Milanovich, Lafayette, CA (US); Klaus Willeke, Cincinnati, OH (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/116,375

(22) Filed: Apr. 3, 2002

(51) Int. Cl.$^7$ ................................................. G01N 1/40
(52) U.S. Cl. ................................ 73/863.21; 73/863.22; 73/863.25; 73/28.04; 55/355; 209/17
(58) Field of Search ........................... 73/863.21, 863.22, 73/863.25, 863.41, 863.51, 863.71, 863.88, 28.01, 28.04, 28.05; 55/355; 209/13, 17, 18

(56) References Cited

U.S. PATENT DOCUMENTS

| 4,972,957 | A | * | 11/1990 | Liu et al. ..................... 209/143 |
| 5,040,424 | A | | 8/1991 | Marple et al. ............ 73/863.22 |
| 5,119,684 | A | * | 6/1992 | Pike ........................ 73/863.22 |
| 5,783,756 | A | | 7/1998 | Xiong et al. .............. 73/863.23 |
| 6,267,016 | B1 | * | 7/2001 | Call et al. ................. 73/863.22 |

FOREIGN PATENT DOCUMENTS

WO       WO 00/16064 A1    3/2000    ............ G01N/1/24

* cited by examiner

Primary Examiner—Hezron Williams
Assistant Examiner—David A. Rogers
(74) Attorney, Agent, or Firm—L. E. Carnahan; Alan H. Thompson

(57) ABSTRACT

A high air volume to low liquid volume aerosol collector. A high volume flow of aerosol particles is drawn into an annular, centripetal slot in a collector which directs the aerosol flow into a small volume of liquid pool contained is a lower center section of the collector. The annular jet of air impinges into the liquid, imbedding initially airborne particles in the liquid. The liquid in the pool continuously circulates in the lower section of the collector by moving to the center line, then upwardly, and through assistance by a rotating deflector plate passes back into the liquid at the outer area adjacent the impinging air jet which passes upwardly through the liquid pool and through a hollow center of the collector, and is discharged via a side outlet opening. Any liquid droplets escaping with the effluent air are captured by a rotating mist eliminator and moved back toward the liquid pool. The collector includes a sensor assembly for determining, controlling, and maintaining the level of the liquid pool, and includes a lower centrally located valve assembly connected to a liquid reservoir and to an analyzer for analyzing the particles which are impinged into the liquid pool.

21 Claims, 1 Drawing Sheet

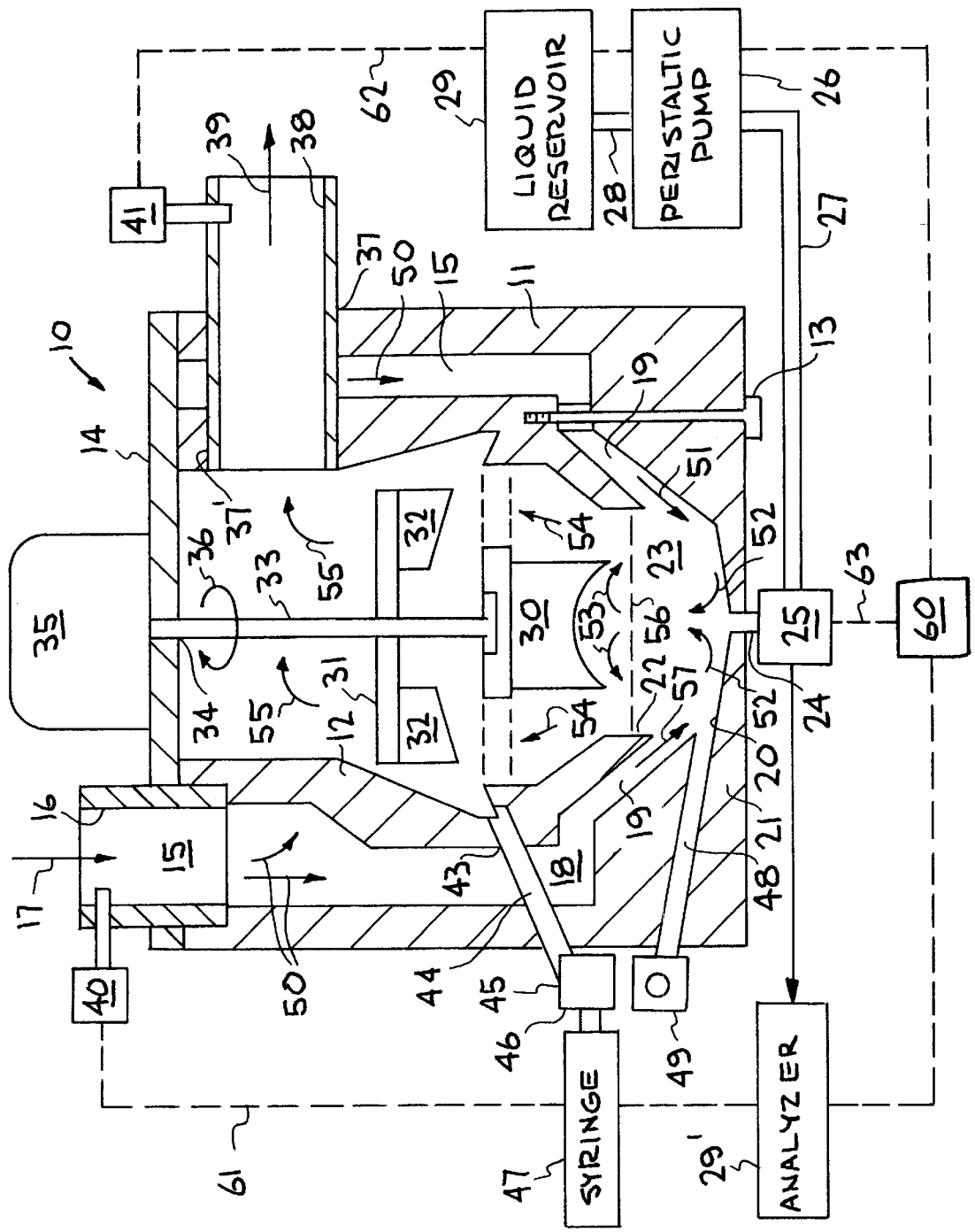

HIGH AIR VOLUME TO LOW LIQUID VOLUME AEROSOL COLLECTOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to air sampling (collection) devices, particularly to portable air sampling systems for the rapid detection and analysis of pathogenic organisms, and more particularly to a portable or stationary high air volume to low liquid volume collector for aerosol particles.

As the threat of biological weapons increases, both in military theaters and civilian populations, the need for portable or stationary systems for the rapid detection and analysis of pathogenic organisms becomes increasingly important. The first step in any system for detection and characterization of biological agents is a sample collector. This can take on the simple form of a cotton swab for solid surfaces, or as in the case of airborne pathogens, an aerosol sample collector is used to collect and concentrate airborne particulate into a liquid sample volume for subsequent preparation and analysis. An aerosol sampler is the most appropriate for continuous monitoring scenarios, where repeated swabbing of settled particles is impractical. Most commercial samplers now available for field use are large, power consuming, and produce collected sample into large volumes of liquid, typically >10 mL. Emerging miniature detection systems analyze much smaller sample volumes, typically <250 $\mu$L. When using the presently available air samplers, the sample volume must be "sub-sampled", effectively diluting the sample, resulting in a loss of sensitivity of detection. Thus, there is a need for a collector which will collect particulate at a high airflow and yet utilize a low liquid volume.

The present invention provides a solution to the above need by providing a collector which can collect airborne particulate at a high air flow rate and yet has been designed so that the resultant delivered liquid volume is 100–300 $\mu$L, preferably only 200 $\mu$L or less. This invention also addresses the problem of dilution because of sub-sampling. The size, weight and low power specifications of this aerosol sampler will closely match the current state-of-the-art in pathogen detection systems and ease the deployment in remote locations. The collector of this invention utilizes high air volume to low liquid volume (preferably 200 $\mu$L) for aerosol particles.

SUMMARY OF THE INVENTION

It is an object of the present invention to provide a high air volume, low liquid volume aerosol collector.

A further object of the invention is to provide a collector for aerosol particles having a high volume flow wherein the particles are drawn into a small volume of liquid (e.g., 200 microliter).

Another object of the invention is to provide a small, low power, high efficiency air sampling or collection device.

Another object of the invention is to provide a portable or stationary high air volume to low liquid volume collector for use with biological or other airborne material collection.

Another object of the invention is to provide an aerosol collector wherein a high volume flow of aerosol particles is drawn into an outer annular slot in the collector and is directed into a small volume of liquid located in a central lower section of the collector, and is provided with means for preventing loss of the collecting liquid and means for controlling the volume of the collecting liquid.

Other objects and advantages will become apparent from the following description and accompanying drawing. The invention is a high air volume to low (100–300, preferably 200 $\mu$L) liquid volume aerosol collector. A high volume flow of aerosol particles (e.g., 225 Lpm) is drawn into an annular, centripetal slot (e.g., 1 to 2 mm wide) located in an outer portion of a collector housing, and which directs the aerosol flow into a small volume (e.g., 200 $\mu$L) of collection liquid located in a lower central portion of the housing. The annular jet of air impinges into the collection liquid pool, imbedding the airborne particles therein in the liquid. The air jet passes through the collection liquid and is discharged from the housing via an upper side opening. The collection liquid continuously circulates by moving to the center of the collector housing, then upwardly, and through assistance by a rotating deflector plate falls back onto the liquid pool above the impinging air jet. Any liquid droplets escaping with the effluent air are captured and moved back toward the liquid pool by a rotating mist eliminator placed above the liquid pool. As liquid is evaporated from the collecting liquid due to the airflow, the required makeup liquid is continuously added through a drain port at the bottom of the collection liquid pool. The amount of makeup liquid is calculated by computer from the difference in the relative humidity measured at the collector air inlet and outlet. To maintain the appropriate amount of collecting liquid, the liquid collected by the mist eliminator is drained back down through a sensor, which measures the liquid flow through it. The sensor can also be used to measure whether the collecting liquid level in the collector is higher or lower than the height of the sensor when the airflow is turned off. This will then activate additional liquid inflow or reduction in inflow. A syringe may be used to extract the liquid above the desired final collecting liquid volume. The liquid can then be drained back in so that the collector can be operated until the liquid has evaporated to the desirable final collecting liquid volume, e.g., 200 microliter.

BRIEF DESCRIPTION OF THE DRAWING

The accompanying drawing, which is incorporated into and forms a part of the disclosure, illustrates an embodiment of the invention, and, together with the description, serves to explain the principles of the invention.

The single FIGURE is a partial cross-section at view of an embodiment of an aerosol collector made in accordance with the invention.

DETAILED DESCRIPTION OF THE INVENTION

The present invention involves an aerosol particle collector having a high air volume to low liquid volume. The collector is small, has low power consumption, with high efficiency, and thus is useful as a portable or stationary field air sampling device. Since the collector is small, it can be utilized in portable biological weapons agent detection systems in conjunction with polymerase chain reaction (PCR) flow cytometry, and electrophoresis. While the invention is useful for most environmental sampling, the illustrated embodiment has been designed primarily for use with biological material collection. Because of the collector's small size (typically 10 cm×10 cm×20 cm) and low weight (typically 0.5 Kg to 1.0 Kg), the collector can be used to sample unconfined spaces such as found in aircraft or subway systems.

Referring now to the drawing, an embodiment of a high air volume to low liquid volume aerosol collector is illustrated in cross-section, with auxiliary components being shown by block diagram with legends. As shown, the collector includes a housing generally indicated at 10 which includes an outer wall assembly 11 and an inner wall assembly 12 mounted within outer wall assembly 11 via bolts 13, only one shown. The housing 10 includes a top plate 14 which extends across upper portions of the outer and inner wall assemblies 11 and 12, secured by screws, etc., not shown. Wall assemblies 11 and 12 are positioned to define an annular, centripetal slot 15 which is in communication with an port 16 in top plate 14, through which inlet air indicated by arrow 17 passes. Slot 15 communicates via an opening 18 and a tapered passage 19 between the lower end of inner wall assembly 12 and outer wall assembly 11, with a lower central interior section 20 formed by a bottom wall 21 of outer wall assembly 11 and an opening 22 having a width of 1 to 2 mm in the lower end of inner wall assembly 12. Interior section 20 defines a chamber in which a collecting liquid pool 23 is located. Bottom wall 21 includes a centrally located opening or drain port 24 connected to a valve assembly 25 which can be connected to a peristaltic pump 26 via connector line 27 and which is connected via a line 28 to a liquid reservoir 29, or to an analyzer 29', as indicated by arrow. Mounted within inner wall assembly 12 and above opening 22 are a deflector plate 30 and a mist eliminator 31 having a plurality of blades 32, each of deflector plate 30 and mist eliminator 31 being mounted to a vertically extending shaft 33 which passes through an opening 34 in top plate 14 and connected to a motor 35 mounted on top plate 14, for rotation of shaft 33 as indicated by arrow 36, with rotor components 30 and 31. Wall assemblies 11 and 12 include openings 37 and 37', respectively, in which a port 38 is mounted, and which functions as an air outlet as indicated by arrow 39. Ports 16 and 38 are provided with relative humidity measurement devices 40 and 41. An inner surface of inner wall assembly 12 is provided with an annular groove 42 and a connecting opening or drain hole 43 in which a tube or line 44 is mounted and which extends through an opening 45 in outer wall assembly 11 and connected to a valve assembly 46 within which is mounted a syringe 47. Outer wall assembly 11 is provided with a passage 48 connected to a liquid sensor 49, with sensor being connected to valve assembly 46.

In operation, a high volume of aerosol particles (e.g., 225 Lpm) is drawn into annular slot 15 as indicated by flow arrows 50, which directs the aerosol flow through opening 18 and 19 into the small volume of collecting liquid pool 23 as indicated by flow arrows 51. The annular jet of air 50-51 impinges into the liquid 23, imbedding therein airborne particles contained in the annular jet of air 50–51. The collecting liquid 23 continuously circulates by moving to the center line of chamber 22 as indicated by arrows 52, then upwardly, and through assistance by the deflector plate 30 back into the collecting liquid pool 23, as indicated by arrows 53. Any liquid droplets escaping with the effluent air, indicated by arrows 54 are captured and moved back toward the liquid pool 23 by mist eliminator 31 wherein the blades 32 expel the droplets toward the surrounding wall (inner surface of inner wall assembly 12). The air flow passes through the interior as indicated by arrows 55 and discharged via outlet port 38 as indicated by arrow 39. The liquid is collected by the groove 42, which is drained via opening 43, tube 44, opening 45, valve assembly 46, sensor 49 and passage 48 into the chamber 20 containing collecting liquid 23. The swirling motion helps to move the collected liquid droplets in the annular groove 42 toward the drain hole or opening 43. As liquid is evaporated from the collecting liquid pool 23 due to the airflow, the required makeup liquid is continuously added through the drain port 24 located at the bottom of the collecting liquid pool 23 from liquid reservoir 29 via valve assembly 25, line 27, pump 26 and line 28. The amount of makeup liquid is calculated by computer 60 from the difference in relative humidity measured at the collector inlet port 16 and outlet port 38 via devices 40 and 41, as indicated by dash lines 61 and 62, the computer being adapted to control valve assembly 25, as indicated by dash line 63. To maintain the appropriate amount of collecting liquid indicated by a liquid level 56 in liquid pool 23, the liquid collected by the mist eliminator 31 and annular groove 42 is drained back down via tube 44, valve assembly 46 through liquid sensor 49, which measures the liquid flow through it. The sensor 49, as pointed out above, can also be used to measure whether the liquid level 56 is higher or lower than the height of the sensor 49 when the airflow is turned off. This will then activate additional liquid inflow or reduction in inflow via the sensor 49 being operatively connected to the computer for activation of valve assembly 25. The syringe 47 may be used to extract the liquid above the desired final liquid volume by activation of valve assembly and liquid flow via passage 48. The amount of excess liquid can be measured and this liquid can then be drained back into the liquid pool 23 as needed, so that the collector can be operated until the liquid has evaporated to the desirable final liquid volume, e.g., 200 microliter. The final liquid volume or pool 23 (with the maximum concentration of collected particles) is then analyzed via activation of valve assembly 25 to connect chamber 20 with an analyzer 29' by one more analysis techniques, such as PCR.

While a specific embodiment of the collector has been described and illustrated to exemplify and teach the principles of the invention, such is not intended to be limiting. Modifications and changes may become apparent to one skilled in the art, and it is intended that the invention be limited only by the scope of the appended claims.

What is claimed is:

1. In an aerosol sample collector for continuous monitoring of airborne pathogens utilizing a liquid to collect and concentrate airborne pathogens for subsequent preparation and analysis, the improvement comprising:
   a housing having a hollow central section,
   a collecting liquid located in a lower section of said central section of said housing,
   said collecting liquid having a volume not greater than about 100–300 microliters, and
   means for maintaining the collecting liquid at a volume not greater than about 100–300 microliters.

2. The improvement of claim 1, wherein said means includes a first fluid passageway located in said housing and above said collecting liquid, a second fluid passageway located in said housing and in communication with said collecting liquid, a valve assembly located external of said housing and connected to said first fluid passageway, and a liquid sensor located external of said housing and connected to said second fluid passageway.

3. The improvement of claim 2, wherein said means additionally including a syringe operatively connected to said valve assembly.

4. The improvement of claim 2, wherein said means additionally includes a collecting liquid reservoir and a second valve assembly mounted in said housing adjacent said collecting liquid therein.

5. The improvement of claim 4, wherein said means additionally includes a computer for controlling said second valve assembly.

6. The improvement of claim 1, additionally including means for swirling said collecting liquid in a central upward and outward direction.

7. The improvement of claim 1, additionally including means for preventing liquid droplets of said collecting liquid from discharging from said housing.

8. The improvement of claim 7, additionally including a groove in said housing adjacent said means for preventing discharge of said liquid droplets, said groove being connected to said means for maintaining the collecting liquid at a volume not greater than about 100–300 microliters.

9. A high air volume to low liquid volume aerosol collector, comprising:

a housing having an outer wall assembly and an inner wall assembly, said inner wall assembly being mounted within and spaced from said outer wall assembly to define an air flow passage therebetween, said housing additionally having a top cover plate extending over said outer and said inner wall assemblies, said cover plate having a port therein through which inlet air is directed into said airflow passage, said outer an d inner wall assemblies having a port through which air is discharged from said housing, said housing containing a quantity of collecting liquid located in a lower central section of said outer and inner wall assemblies, means for controllably supplying liquid to said quantity of collecting liquid, and means for controlling the volume of said collecting liquid.

10. The aerosol collector of claim 9, additionally including a rotatable deflector plate mounted within said inner wall assembly and located above said quantity of collecting liquid.

11. The aerosol collector of claim 10, additionally including a rotatable mist eliminator located within said inner wall assembly and above said rotatable deflector plate.

12. The aerosol collector of claim 11, additionally including a motor mounted to rotate said rotatable deflector plate and said rotatable mist eliminator.

13. The aerosol collector of claim 12, wherein said motor is located externally of said housing.

14. The aerosol collector of claim 9, wherein said means for controlling supplying liquid to said quantity of collecting liquid includes a valve assembly operatively mounted to connect a liquid reservoir with said quantity of collecting liquid, and means for controlling said valve assembly in response to the difference in relative humidity measured at said port in said top cover plate and said port in said outer and inner wall assemblies.

15. The aerosol collector of claim 9, wherein said means for controlling the volume of said collecting liquid includes a liquid sensor operatively connected to said quantity of collecting liquid and to a point in said inner wall assembly located above said quantity of collecting liquid.

16. The aerosol collector of claim 15, wherein said means for controlling the volume of said collecting liquid additionally includes a valve assembly operatively connected to said liquid sensor.

17. The aerosol collector of claim 16, wherein said means for controlling the volume of said collecting liquid additionally includes a syringe operatively connected to said valve assembly.

18. The aerosol collector of claim 15, wherein said inner wall assembly is provided with an annular groove on an inner surface thereof, said groove being in fluid communication with said point in said inner wall assembly located above said quantity of collecting liquid.

19. The aerosol collector of claim 9, wherein said quantity of collecting liquid is not greater than about 200 microliters, and wherein said collector is portable.

20. The improvement of claim 1, wherein said collecting liquid has a volume of about 200 microliters.

21. The improvement of claim 8, wherein said collecting liquid volume is about 200 microliters.

* * * * *